United States Patent
Hadvary et al.

(10) Patent No.: US 6,685,675 B1
(45) Date of Patent: *Feb. 3, 2004

(54) MEDICAL DEVICE ADHERING TO THE SKIN

(75) Inventors: Paul Hadvary, Biel-Benken (CH); Hansjörg Tschirky, Ettingen (CH)

(73) Assignee: Hoffmann-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,279
(22) PCT Filed: May 10, 1996
(86) PCT No.: PCT/EP96/02010
§ 371 (c)(1),
(2), (4) Date: Nov. 14, 1997
(87) PCT Pub. No.: WO96/37244
PCT Pub. Date: Nov. 28, 1996

(30) Foreign Application Priority Data
May 22, 1995 (CH) .............................................. 1487-95

(51) Int. Cl.⁷ ................................................. A61M 5/32
(52) U.S. Cl. ...................................................... 604/180
(58) Field of Search .......................... 604/19, 131, 304, 604/307, 308, 174, 179, 180, 20–21; 602/52, 57; 128/DIG. 6, 26; 428/40.1; 427/207.1, 208, 208.4

(56) References Cited

U.S. PATENT DOCUMENTS

| | | | | |
|---|---|---|---|---|
| 3,712,304 A | * | 1/1973 | Marsan | 128/283 |
| 4,392,853 A | * | 7/1983 | Muto | |
| 4,519,793 A | * | 5/1985 | Galindo | |
| 4,809,705 A | * | 3/1989 | Ascher | 128/710 |
| 4,911,707 A | * | 3/1990 | Heiber et al. | |
| 5,348,007 A | * | 9/1994 | Hitti | |
| 5,545,143 A | * | 8/1996 | Fischell | |

FOREIGN PATENT DOCUMENTS

GB  1021145  * 3/1964

* cited by examiner

Primary Examiner—LoAn H. Thanh
(74) Attorney, Agent, or Firm—George W. Johnston; Patricia S. Rocha-Tramaloni; Lyman H. Smith

(57) ABSTRACT

The present invention relates to a medical device adhering to the skin comprising a housing with a rigid base fixable on a patient's skin by means of an adhesive layer which has an adhesive surface, essentially co-extensive with the base, contacting the skin and which is fixed to the base by a reduced surface in comparison to the adhesive surface contacting the skin.

2 Claims, 2 Drawing Sheets

MEDICAL DEVICE ADHERING TO THE SKIN

BACKGROUND

1. Field of the Invention

The invention relates to a medical device comprising a housing with a rigid base which is fixed on the patient's skin by means of an adhesive layer for temporary wearing on the body.

2. Related Art

Devices of this kind are, for example, transducers or transdermal injection or infusion devices, etc. In order to fix them, the application surface is provided with an adhesive coating which is usually annular and has an outside diameter corresponding to the device.

The adhesive layers usually adhere to the skin very well, but if the device is worn for any length of time and is subject to appreciable movement the adhesive layer becomes detached starting from the edge.

Attempts have been made to counteract this by increasing the adhesive surface, so that its outside diameter is larger than that of the device. However, this also has disadvantages, so that no satisfactory solution of the problem has hitherto been found.

The object of the invention is to solve this problem.

SUMMARY OF THE INVENTION

To this end, according to the invention, the adhesive layer is fixed to the device by a reduced surface in comparison with the adhesive surface facing the skin. Preferably, this gives an outer annular zone of the adhesive layer where the latter is not connected to the device.

DETAILED DESCRIPTION OF THE INVENTION

One exemplified embodiment of the invention is described hereinafter with reference to the accompanying drawing.

Figure 1:
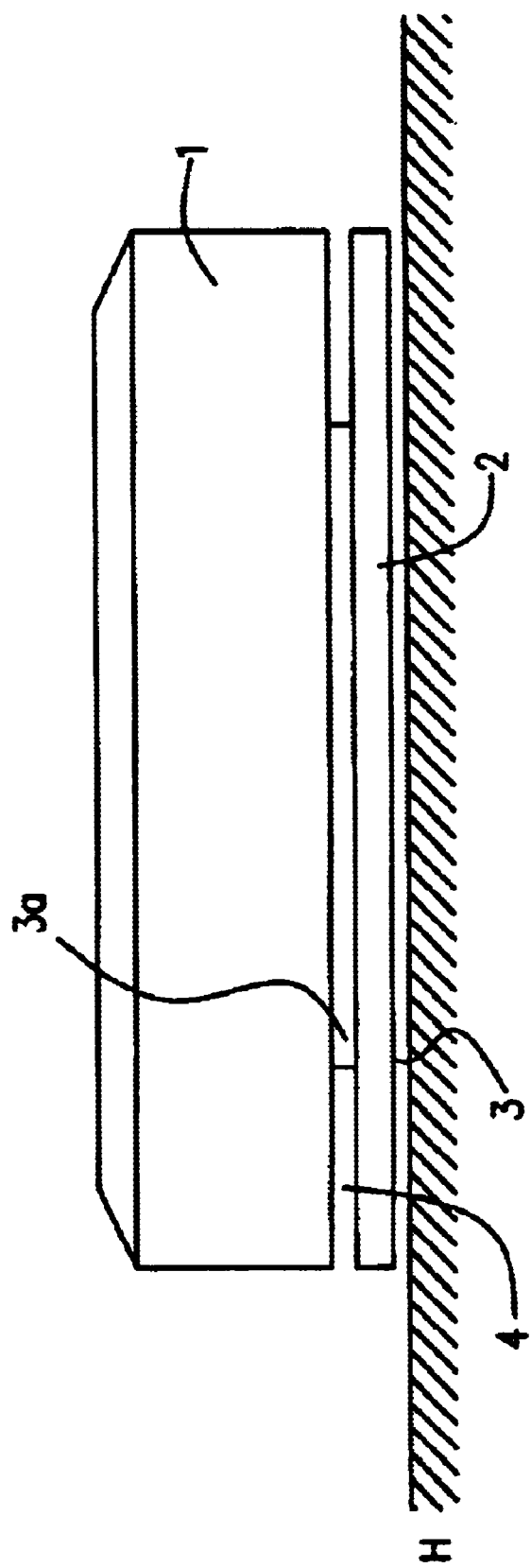
FIG. 1 shows a cross sectional view of the medical device of the present invention.
Figure 2:
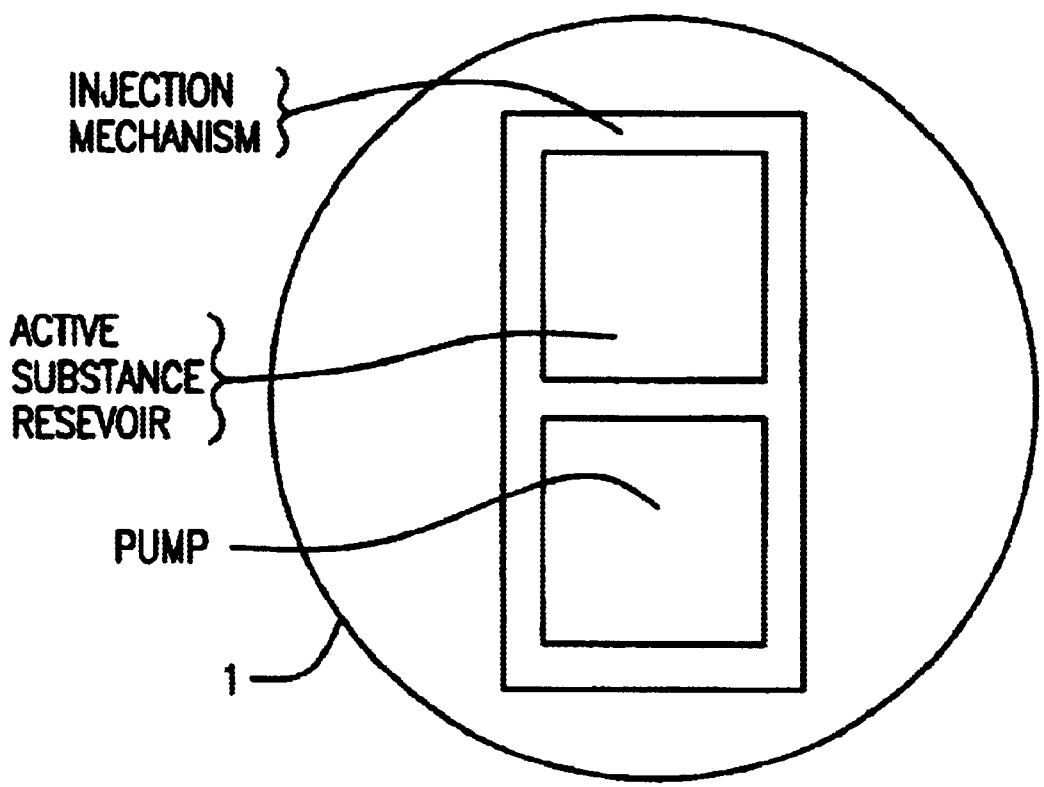
FIG. 2 shows a schematic representation of the housing of the medical device of the present invention.

FIGS. 1 and 2 are diagrams of a transdermal injection system worn on the patient's skin for a given time, e.g. a number of days. The injection mechanism including the pump and active substance reservoir is located in a housing 1. The latter is fixed on the patient's skin H by means of an adhesive layer 2. The adhesive surface 3 of the adhesive layer is of the same size as the underside of the housing 1. The surface by which the adhesive layer is fixed on the housing 1 on the side remote from the adhesive surface 3 is smaller than the latter. The adhesive layer a is not connected to the housing 1 in an outer zone 4. This zone is annular and extends from the outer edge inwardly by about 5 to 10 mm.

It has been found that this configuration does not result in detachment from the skin even when worn for long periods and subjected to extensive movement.

What is claimed is:

1. A transdermal injection system for administering an active substance to a patient adapted to be affixed to a skin surface of the patient including a housing, said housing including an injection mechanism having a pump and an active substance reservoir therein, said housing defining a rigid base having a size, and one adhesive layer interposed between said rigid base of said housing and adapted for adhering to a patient's skin for adhesively affixing said injection system to the patient's skin wherein the improvement comprises:

a first adhesive surface of said one adhesive layer adjacent to and adapted to be adherent to the skin of the patient having an equivalent size to said size of said rigid base of said housing, and a second adhesive surface of said adhesive layer adjacent to and adherent to said rigid base of said housing, wherein said second adhesive surface having a reduced surface in comparison with said first adhesive surface, wherein said reduced surface defines an annular zone extending from an edge of said reduced surface a distance between about five to about ten mm to an outer edge of said housing, and wherein said adhesive layer is not connected to said housing in said annular zone, thereby capable of substantially reducing an inadvertent detachment of said first adhesive surface from the skin of the patient.

2. A transdermal injection system for administering an active substance to a patient adapted to be affixed to the skin of the patient's body comprising:

a housing including an injection mechanism having a pump and an active substance reservoir therewithin, said housing defining a rigid base having a size;

one adhesive layer interposed between said rigid base of said housing and adapted for adhering to the patient's skin for adhesively affixing said injection system, wherein a first adhesive surface of said adhesive layer, adjacent to and adapted to be adherent to the skin of the patient, has an equivalent size to said size of said rigid base of said housing; and a second adhesive surface of said adhesive layer adjacent to and adherent to said rigid base of said housing, wherein said second adhesive surface having a reduced surface in comparison with said first adhesive surface, wherein said reduced surface defines an annular zone extending from an edge of said reduced surface a distance between about five to about ten mm to an outer edge of said housing, and wherein said adhesive later is not connected to said housing in said annular zone, thereby capable of substantially reducing an inadvertent detachment of said first adhesive surface from the skin of the patient.

* * * * *